(12) United States Patent
Poormand (10) Patent No.: US 10,278,571 B2
(45) Date of Patent: May 7, 2019

(54) LARYNGOSCOPES

(71) Applicant: FLEXICARE (GROUP) LIMITED, Mountain Ash (GB)

(72) Inventor: Khashayar Poormand, Mountain Ash (GB)

(73) Assignee: FLEXICARE (GROUP) LIMITED, Mountain Ash (GB)

( * ) Notice: Subject to any disclaimer, the term of this patent is extended or adjusted under 35 U.S.C. 154(b) by 203 days.

(21) Appl. No.: 15/228,474

(22) Filed: Aug. 4, 2016

(65) Prior Publication Data

US 2018/0008137 A1 Jan. 11, 2018

(30) Foreign Application Priority Data

Jul. 6, 2016 (GB) .................................. 1611773.1

(51) Int. Cl.
*A61B 1/267* (2006.01)
*A61B 1/07* (2006.01)
(Continued)

(52) U.S. Cl.
CPC .......... *A61B 1/267* (2013.01); *A61B 1/00032* (2013.01); *A61B 1/00103* (2013.01); *A61B 1/06* (2013.01); *A61B 1/07* (2013.01)

(58) Field of Classification Search
CPC .................................. A61B 1/07; A61B 1/267
(Continued)

(56) References Cited

U.S. PATENT DOCUMENTS 3,629,793 A * 12/1971 Ettischer ............ G03B 15/0442
362/157
7,909,759 B2 † 3/2011 Pecherer
(Continued)

FOREIGN PATENT DOCUMENTS

| GB | 2 385 793 | 9/2003 |
|---|---|---|
| GB | 2491189 | 11/2012 |
| JP | 2008289668 | 12/2008 |

OTHER PUBLICATIONS

Search Report for GB1611773.1 dated Jan. 4, 2018.
(Continued)

*Primary Examiner* — Anu Ramana
(74) *Attorney, Agent, or Firm* — Stephen J. Weyer; Stites & Harbison, PLLC (57) ABSTRACT

A laryngoscope has a blade pivoted to a handle, and a light emitter lamp on the blade powered from a battery power source. A block formation at the rear end of the blade, at which it is pivoted to the head of the handle, incorporates a power source housing for the battery. The power source housing has a cover flap which cannot be opened in the operating position of the blade, but can be opened for removal of the power source in the folded position, or with the blade detached. This facilitates disposal and recycling. Electrical connectors lead from the power source housing to the light emitter lamp, and the rear end block of the blade has an external switch actuator which engages the head of the handle when the blade is extended to turn on the lamp. The power source, electrical connectors and light emitter may be combined into a discrete lighting module casing incorporated in the blade.

17 Claims, 5 Drawing Sheets

(51) Int. Cl.
*A61B 1/00* (2006.01)
*A61B 1/06* (2006.01)

(58) Field of Classification Search
USPC ........ 600/185, 188, 191, 193, 196, 197, 199
See application file for complete search history.

(56) References Cited

U.S. PATENT DOCUMENTS

| | | |
|---|---|---|
| 2005/0159649 A1 | 7/2005 | Patel |
| 2006/0189847 A1 | 8/2006 | Yee et al. |
| 2010/0179387 A1 | 7/2010 | Bird et al. |
| 2014/0371536 A1 | 12/2014 | Miller et al. |
| 2015/0051447 A1 | 2/2015 | Swift |
| 2017/0150878 A1† | 6/2017 | Swift |
| 2017/0202447 A1* | 7/2017 | Pecherer ................ A61B 1/267 |

OTHER PUBLICATIONS

International Search Report, and the Written Opinion, Application No. PCT/EP2017/066746, dated Sep. 27, 2017, 13 pages.
http://www.flexicare.com/images/downloads/BritePro%20Solo.pdf, 4 pages, Flexicare, Britepro Solo, Jun. 5, 2015 (saved date).
http://www.carefusion.com/Documents/brochures/anesthesia-delivery/VS_GreenLightlaryngoscope-system_BR_EN.pdf, 2 pages, Carefusion; Sep. 17, 2014 (saved date).
http://www.ms21.co.uk/wp-content/themes/ms21/pdfs/Timesco-Optima-Laryngoscopes.pdf, 2 pages, Timesco Surgical + Medical; Feb. 18, 2010 (saved date).
http://www.ms21.co.uk/wp-content/themes/ms21/pdfs/Timesco-suap.pdf, 9 pages, Timesco Surgical + Medical; Oct. 15, 2004 (saved date).
https://www.welchaliyn.com/content/dam/welchallyn/documents/sapdocuments/LIT/800017/80017344LITPDF.pdf, 4 pages, Welch Allyn; Jun. 6, 2013 (saved date).
Teleflex, Truphatek Laryngoscope Portfolio, 2015, published as early as Mar. 22, 2016 at https://www.truphatek.com/files/files/Truphatek%20Brochure%202015.pdf.†

* cited by examiner
† cited by third party

LARYNGOSCOPES

FIELD OF THE INVENTION

This invention has to do with laryngoscopes and blades for laryngoscopes.

BACKGROUND

Laryngoscopes are widely used to assist with tracheal intubation. A conventional laryngoscope consists of a handle and a blade connected pivotably at the head of the handle. The blade is movable between an operative position, in which it projects out laterally, and a folded position in which it lies down against the side of the handle. In typical use a clinician standing above/behind the head of the supine patient holds the laryngoscope in one hand, blade-downwards with the blade underside away from them, and the breathing tube in the other hand. The blade is put down the patient's throat and turned and lifted by forcible tilting of the handle to move the tongue and epiglottis out of the way. The blade carries a light. The breathing tube is slid in along the upper side of the blade, which may be shaped to guide this. Visibility—assisted by the light—is critical to ensure that the tube has indeed entered the trachea. Note: the terms upper side and underside are used in relation to the blade as it would be with the handle vertical and head upwards, and the blade projecting in the operating position. During actual use as described, the upper side would be inclined down.

Intubation is almost always urgent. For this reason although many blade designs exist clinicians generally prefer to use a familiar one. Care is needed not to damage the front teeth by using them as a reaction point for the rear end of the blade when lifting the tongue. With the urgent situation and substantial force applied, there is a possibility of minor abrasions in the mouth or throat so sterility is important. Many laryngoscopes are now "single use": sometimes just the blade and sometimes the entire instrument. Otherwise, a laryngoscope might contribute to carrying infection from the patient to another patient.

Two kinds of light emitter are conventional. Each uses a power source, specifically a battery, in the shaft of the handle. In one kind the head of the handle has an upwardly-directed lamp (bulb or LED) beneath the pivot joint with the blade, and the blade has an optical fibre bundle leading from its rear end to the emitter position towards the tip. Pivoting the handle to the operative position switches on the lamp and presents the proximal end of the optical fibres to the handle lamp so that light is emitted at the front of the blade. In the other kind the light emitter on the blade is itself a lamp, such as a filament bulb or LED, and the blade rear end and handle head have respective contacts which engage when the blade is swung to the operating position to turn on the lamp.

Moulded plastic blades have obvious manufacturing advantages, but limited clinical acceptability because of concerns about bending and breakage. Metal blades are widely used, as single-use blades and in single-use instruments.

Many known laryngoscopes have detachable blades with a standard hook-on fitting to a pivot bar mounted across the head of the handle. A range of blades may be usable with a single handle.

With single-use laryngoscopes, difficulties may arise with disposal regulations. For example a single-use handle may be adapted to prevent removal of the batteries—to prevent repeated use—but this prevents disposal if local laws require recycling of batteries.

THE INVENTION

Our aim herein is to provide new and useful laryngoscopes and laryngoscope blades addressing some of the issues discussed above.

Our proposals relate in general to laryngoscopes of the following type, comprising a handle and a blade. The blade has a front or tip end and a rear end, and a blade body extending between them. The blade body has an underside and an upper side. The handle has a head, and the blade and handle are connected by a pivoted connection between the rear end of the blade and the handle head. The blade is pivotable relative to the handle between an operating position and a folded position. The blade comprises a light emitter directed forward to the tip end, and the laryngoscope includes a power source—generally one or more batteries, electrical connections for causing light to be emitted from the light emitter, and preferably a switch for actuating the light emitter to emit light when the blade is moved to the operating position.

In a first aspect of our proposals, in a laryngoscope of the kind described, the rear end of the blade comprises a housing for the power source. The housing may be defined in a rear end block of the blade which also carries or comprises connector formations for the connection of the blade to the handle. One such connector formation is a pivot engagement formation, such as a pivot pin, or opening for receiving a pivot pin, on or in the end block. Another possible connector formation is a catch formation constituting part of a catch mechanism operating between the blade end and the handle head which has a corresponding catch formation. The head and handle catch formations engage in the operating position of the blade, e.g. with a snap or click action, to inhibit pivoting back to the folded position. This in itself is known; in our proposals one or both of these connector formation types can be provided on a rear end block of the blade which also houses the power source.

The housing may have spaced side walls, with a chamber for the power source defined between them. The respective side walls may carry connector formations as mentioned.

Desirably the housing has a moveable cover, such as a cover flap hinged to the housing wall, operable to open or close an opening through which the power source such as one or more batteries can be put into or removed from the housing. The cover desirably makes a cover catch engagement with the housing wall to hold it closed; forcible deformation of the cover catch mechanism may be needed to release it. We prefer that in the operating position of the blade, a portion of the head of the handle opposes the cover and/or the cover catch mechanism so that the cover cannot open and/or so that the cover catch cannot be released.

In preferred versions, the rear end or rear block formation of the blade has a bottom surface and a rear surface, and the cover constitutes or is comprised in the rear surface. A part of the cover forming the cover catch mechanism may be on the bottom surface, and the bottom surface lies against or closely adjacent to an upward surface of the handle head in the operating position so that it cannot be released. For example the catch mechanism may have interlocking components which, for release, require part of the cover to be deformed outwardly (downwardly, in the operating position).

As mentioned, the blade comprises a light emitter, and this is generally positioned forwardly-directed at an intermediate position on the blade body. Lighting connections extend between the power source housing and the light emitter. In a preferred version the light emitter is a lamp—such as a filament bulb or (preferably) LED—and the lighting connectors are conductive wiring. In an alternative embodiment the light emitter may be the distal end of an optical fibre connector constituting the lighting connector, and leading back to the power source housing where a lamp such as an LED—which may be enclosed—connected to the power source supplies light to a proximal end of the optical fibre connector.

In preferred designs the handle head has opposed laterally spaced upstanding supports and the rear end of the blade, such as a block formation, fits between these supports. A pivot connection, such as by laterally-projecting pin ends, can be made between the blade end or block formation and the supports e.g. towards the front of the handle head. A catch engagement for holding the blade in the operating position can be made between the supports and the blade end or block formation e.g. towards the rear of the head. Thus, preferably in this position the housing of the power source lies between the upstanding supports of the handle head. The handle head may have an upwardly-directed surface such as a generally flat abutment surface between the supports, which closely opposes or abuts a bottom surface of the blade rear end in this position.

A switch, connected to the power source, lighting connections and light emitter, desirably has an external movable switch actuator which engages the handle head selectively in the operating position to operate the actuator and switch on the light. Desirably this switch is on a bottom surface of the blade rear end, as described above in various forms, and meets a corresponding upward or abutment surface of the head of the handle e.g. as described above, for this purpose.

It will be understood that, in this arrangement, all the operative means for lighting are included in the blade itself. The handle need not contain any parts of the lighting system, so that for example concerns about the disposability of batteries need not affect possible disposal of the handle. Conversely, by housing the power source in the rear end of the blade, and especially in one of the preferred ways described, concerns about exposure or escape of the power source or other parts of the lighting system during use can be eliminated. Thus, if a cover for the housing is impossible to open in the operating position, e.g. according to a proposal above, the power source cannot fall out.

Conversely, because the housing may conveniently be adapted for removal or insertion of the power source, the power source can then be removed (with the blade out of the operating position, e.g. in the folded position) so that the entire instrument can be disposed of (without the power source/batteries) in line with prevailing regulations.

Further novel aspects of our proposals relate to the disposition and nature of the lighting system elements.

A laryngoscope of the kind described in which a lighting system, comprising a power source, lighting connections and a light emitter, is entirely comprised in the blade is a further aspect of our proposals. Options and preferences for the components of the lighting system in this aspect may be as suggested above in the first aspect, except that the position and accessibility of the power source in the blade is then not particularly limited although it is preferably as disclosed above.

One preferable proposal is that the blade comprises a main blade body portion and a discrete lighting module fitted to the main blade body portion to complete the blade. The lighting module may comprise a module casing, such as a plastics casing which may desirably be formed in one piece, comprising a power source housing portion and a connector surround portion or stem extending from the power source housing portion towards the light emitter of the lighting module, and surrounding or enclosing lighting connections such as wires or an optical fibre connector extending between the power source and the light emitter. Desirably, as mentioned above, the light emitter is a lamp and the lighting connectors are conductive wires.

The light lighting module generally also comprises a switch mechanism, and an external movable actuator for the switch may be positioned on the power source housing portion of the module, e.g. at a bottom surface thereof. The operation of this may be as described above in the previous aspects.

In a further aspect of our proposals, relevant for both of the previous aspects, a rear end block formation of the blade may consist, in the lateral direction corresponding to the direction of the pivot axis, partly of the power source housing, e.g. of a lighting module as mentioned, and partly of a rear portion of a discrete main blade body portion. A discrete power source housing may be sandwiched between opposed spaced rear plates or side portions of a main blade body portion, the latter also carrying the connector formations. However, for compactness and simplicity we prefer that one side be the discrete power source housing, and the other side be a rearward extension or side plate of the main blade body. That is, the rear block of the blade is a composite of the two discrete elements.

Preferably the main blade body portion comprises a pivot connector portion extending laterally across the power source housing to make the pivot connection across most or all of the blade rear end width. The strength of the main body material is then used for the connection, and the housing can be of weaker material e.g. moulded plastics.

Preferably the blade has a form in which the upper surface has a laterally-directed guide face for guiding intubation, e.g. having a high side (upper flange) and a low side (lower flange) as in the well-known Macintosh blade type, with an upright step wall between. In such a blade the high side of the blade body has clearance beneath it which may constitute a receiving recess for a lighting module to be fitted, with the stem part extending forward underneath the high side of the blade body. The lateral wall may have an opening part-way along the blade—typically nearer to the tip end—through which the lighting connector projects so that the light emitter can shine forward. In a particularly preferred embodiment, which is an independent aspect of proposals here, the laterally-directed wall inclines away from the front-rear direction forward of the emergence of the light emitter, to widen the field of illumination forward of the blade.

The blade, and in particular the main blade body portion in the relevant aspects above, is desirably of metal. It may be press-moulded from sheet as is known or, more preferably, cast or moulded (e.g. from zinc) to maximise the freedom of shape design.

Laryngoscope blades having any of the combinations of features set forth herein are themselves a further aspect of the invention.

The type of handle can be freely chosen, subject to the preferences in the proposals described above. The handle may have a conventional form, i.e. a generally cylindrical rigid piece with a straight main shaft between the head and a foot.

We prefer that the blade be permanently pivoted to the handle, as distinct from a detachable hook-on fitting, but some of the present proposals can be embodied in hook-on blades.

BRIEF DESCRIPTION OF THE DRAWINGS

An embodiment of our proposals is now described by way of example, with reference to the accompanying drawings in which.

DETAILED DESCRIPTION OF THE EMBODIMENT

The illustrated laryngoscope consists of a blade 2 connected to a handle 1 at a pivot connection 3. A handle 1 has a conventional cylindrical body shaft 12 with a flat foot 13, and a head 11 formed with a pair of laterally-spaced upstanding side supports 14, in the form of flat parallel clevis plates, for the connection to the blade 2. The handle may be of metal, with an elastomer grip sleeve. It is hollow, light and contains no electrical components. Between the side supports 14 the head 11 has an upwardly-directed flat abutment surface 15: this is where a conventional laryngoscope would have a lamp for optical fibre illumination, or electrical contacts for a lamp in the blade powered from a battery in the handle.

The blade 2 has a main blade body portion 21 into which a lighting module 22 is fitted, and these components in combination constitute the blade. The blade has a rear end 23, a tip end 24, an underside 25 and an upper side 26. In this embodiment the blade has the popular Macintosh form, but other forms may be used. The rear end of the blade has in the form of a block 27 which fits closely between the handle head side supports 14 to form the pivot connection. The rear end block 27 is constituted by a power source housing 5 (part of the lighting module 22) side by side with a rearward side extension 211 and a lateral pivot extension 212 each being an integral part of the main metal blade body portion 21. The power source housing 5 constitutes about ⅔ of the width of the block 27, and the side blade 211 about ⅓ of the width. However across the front of the power source housing the lateral pivot extension 212 extends nearly the full width of the block.

The power source housing 5 is defined primarily by a moulded plastics module casing component 6, which integrally combines a housing portion 61 defining the power source housing, and a chamber within for the power source 10, and an integral stem surround 62 of tubular form which extends forward along the blade from an integral join 63 at the top of the housing 5, surrounding connector wires 7, to the lamp, typically an LED lamp, constituting a light emitter 8 which is about ⅔ of the distance forward along the blade. The stem surround, wires and lamp constitute a stem of the lighting module.

Along most of its length towards the handle end the blade has a laterally-stepped form comprising an upper flange 265, a lower flange 266 and an upright step wall 264 between them, the upper and lower flanges 265,266 providing upper and lower levels 263,261 of the upper side face 26, and the step wall 264 providing a lateral guide face 262 which, in a known manner, combines with the lower level face 261 to help guide a breathing tube into the trachea in use. Towards the front of the blade the step wall 264 inclines out laterally and has an opening 267 through which projects the tip of the lighting module stem, with the lamp 8. The upper flange 265 continues above this region to cover the stem and then terminates; the final part of the tip has a simple spatulate form as is conventional.

A receiving recess 28 is defined along beneath the upper flange 265 of the blade, and the stem of the lighting module 22 fits along in this recess.

The module casing component 6 may be injection moulded, e.g. from nylon, and is desirably in one piece including the elements of the power source housing 5 to be described below.

First, the connection to the handle is described. A metal pivot pin 31 passes through the side supports 14 and the rear end block 27 of the blade towards the front of the head, through pivot pin holes 141 in the supports 14 and a block pin hole extending mostly through the lateral extension 212 at the rear of the main blade body, but also through a forward extension, lying alongside the blade body extension 212, of a side wall 51 of the moulded power source housing. Since the pivot is made primarily with the extension 212 which is nearly full-width and solid with the metal blade, the connection has high strength. At the same time, it holds the power source housing 5 in position in the blade structure so that it cannot be dislodged.

Rearwardly of the pivot each side support 14 has a catch recess 42, in the form of a rearwardly-open slot, and the corresponding side faces of the blade block 27—one on the power source housing wall 51, the other on the blade body side extension 211—have respective projections 41 in the form of rounded nibs to engage these slots. The rearward opening of the slots is for assembly. In the assembled device, these formations act as a catch mechanism to hold the blade in the operating position. Firm downward pressure on the blade can release it to the folded position. Upward force on the blade—such as in use—does not move it because the flat bottom surface 271 of the end block 27 lies against the flat upward abutment surface 15 of the handle head 11. The power source housing 5 defines, in combination with the blade body side plate 211, a housing chamber which holds a power source 10, typically one or more lithium batteries. The power source 10 is connected to the connector wires 7 and lamp 8 via a switch 9 having an actuator button 91 which projects out from the bottom surface of the blade end block 27. When the blade is moved to the operating position the actuator button 91 is pressed by the abutment surface 15 and switches the lamp on.

The injection-moulded housing portion 61 of the lighting module casing component 6 has a side wall 51 already mentioned, a front wall to restrain the battery and to house the switch 9 and proximal connections of the wires 7, a bottom wall, a top wall incorporating the join 63 and a rear cover flap 55 which is connected to the top wall by an integral moulded hinge (living hinge) and constitutes the rear wall of the housing 5.

Figure 1:
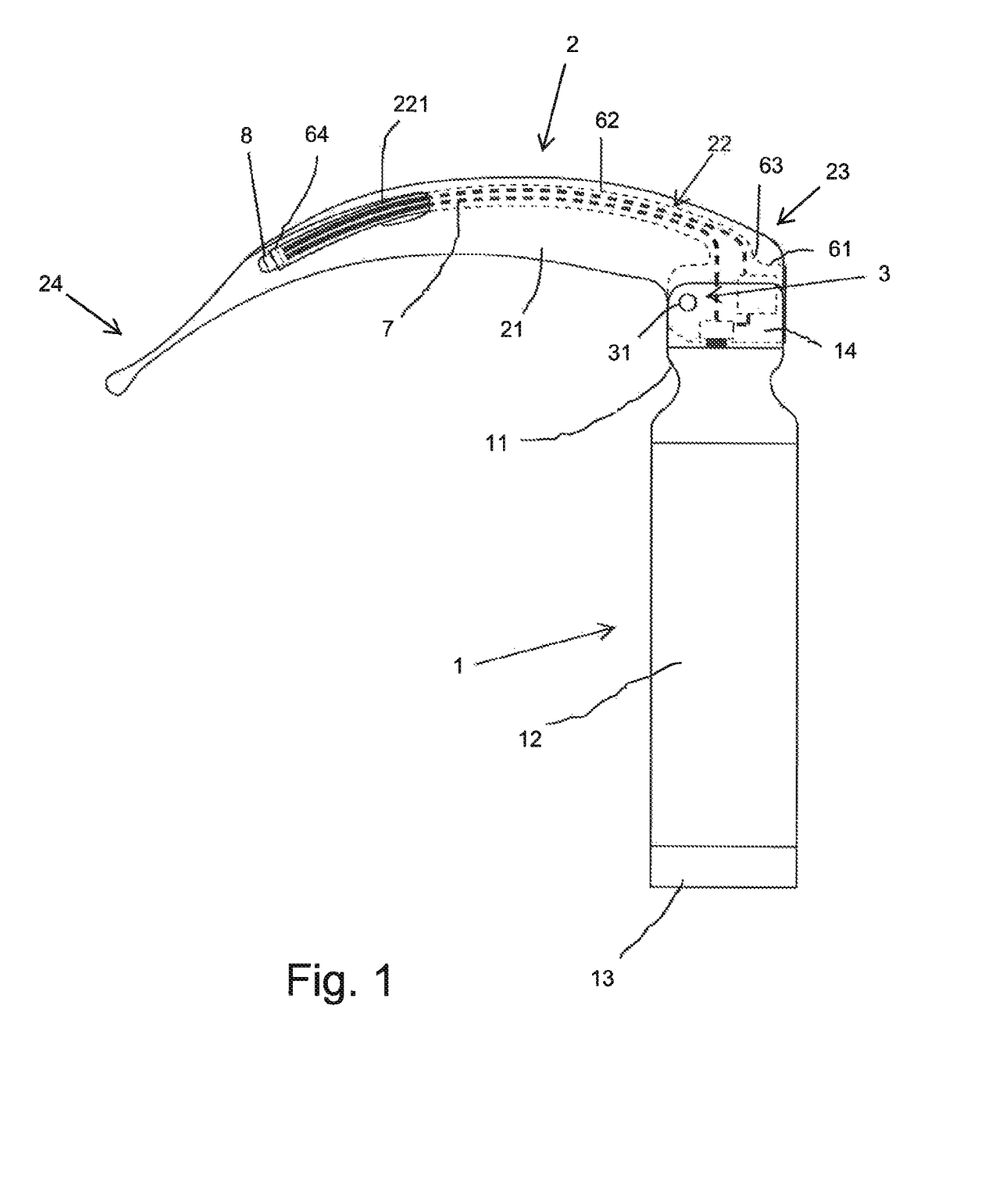
FIG. 1 is a side view of a laryngoscope in the operating position.
Figure 2:
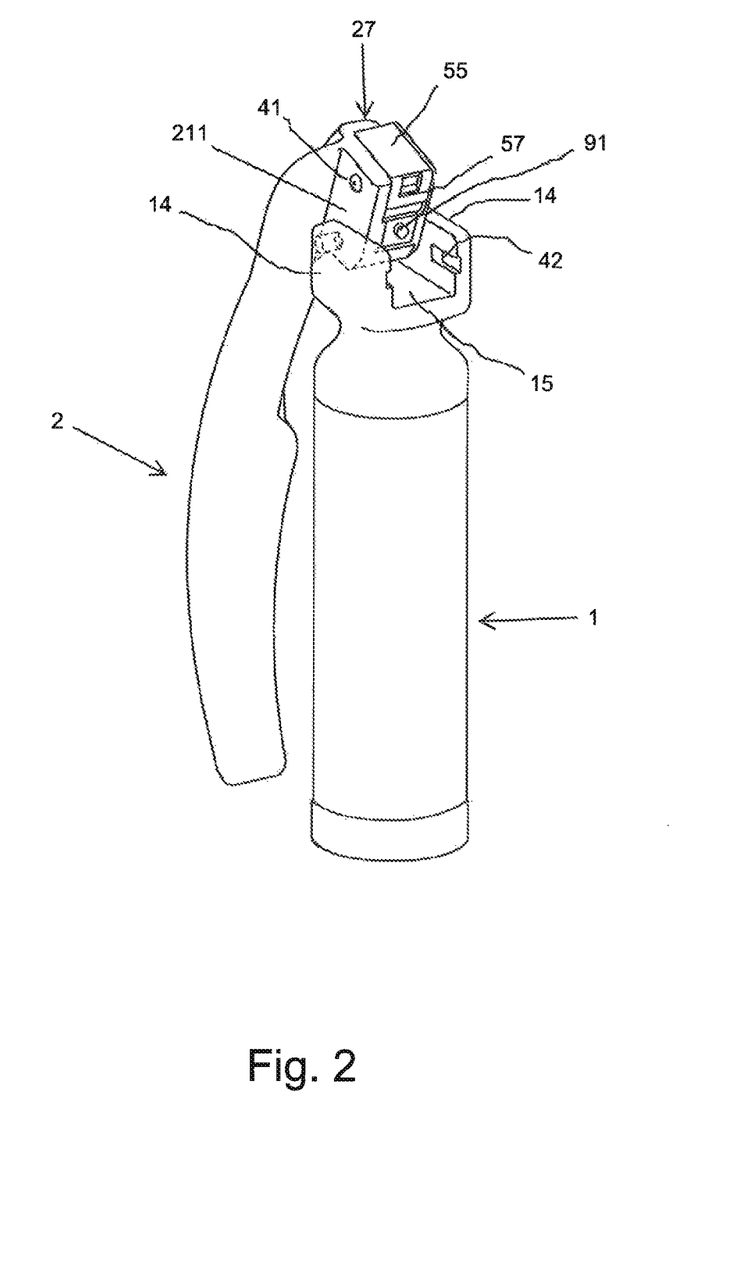
FIG. 2 is an oblique rear view of the laryngoscope in a folded position.
Figure 3:
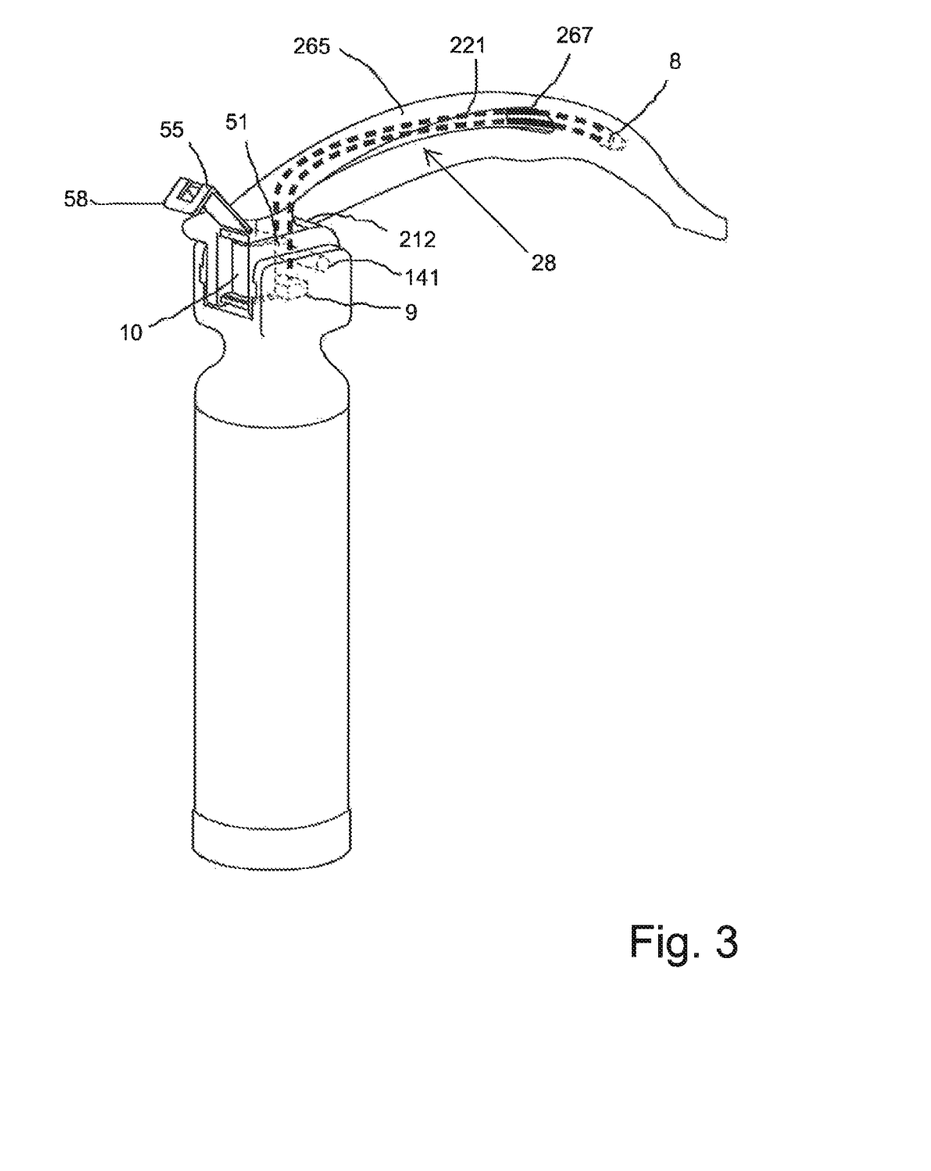
FIG. 3 is an oblique rear view, from the opposite side, of the laryngoscope in the operating position.
Figure 4:
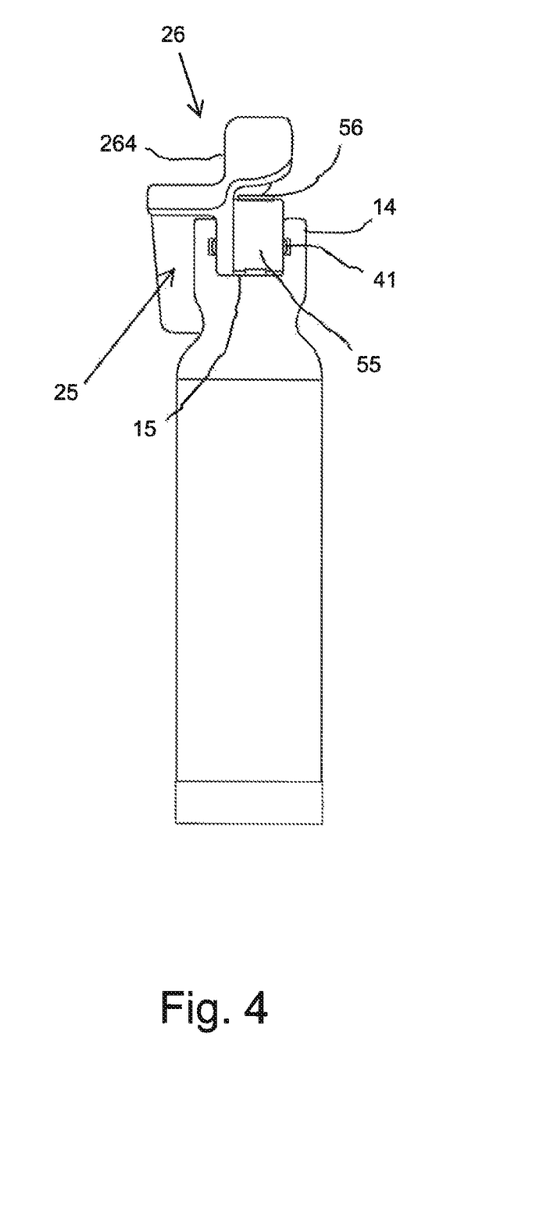
FIGS. 4 & 5 are rear and front views of the laryngoscope in the operating position.
Figure 5:
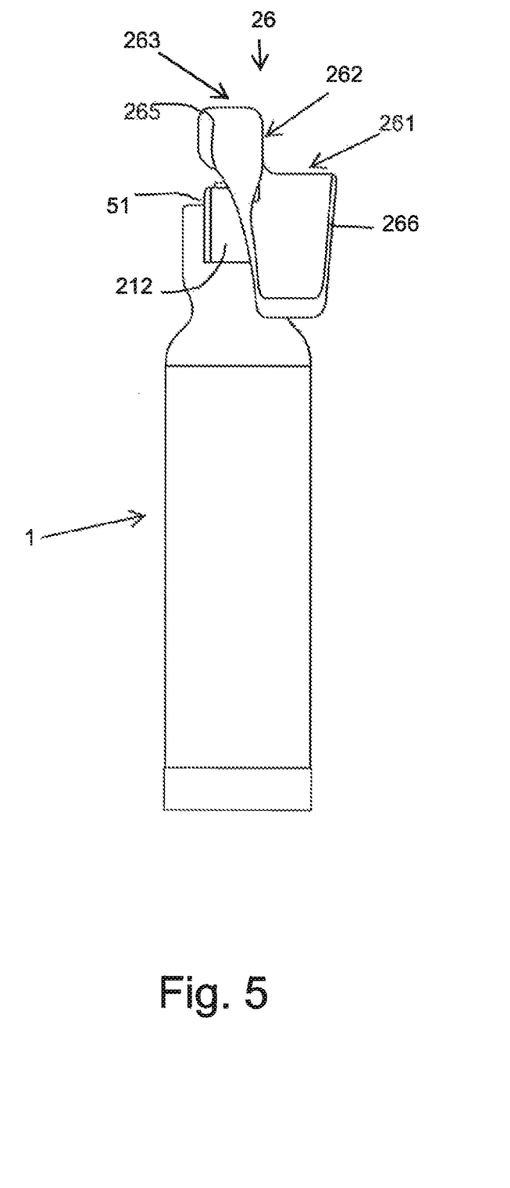

As seen in FIGS. 2 & 3, the cover flap 55 has a lift tab 58 angled round onto the bottom surface of the end block 27, and making a snap engagement 57 with the bottom wall of the housing which can be released by lifting the lift tab 58 e.g. with a finger nail. Thus, while this cover 55 can be open for insertion or removal of a power source 10 before the blade 2 is connected to the handle, or in the folded position of FIG. 2, it cannot be opened in the operating position because the lift tab 58 is held up in snap engagement by the abutment surface 15 of the handle head. [FIG. 3 shows the cover 55 open in the operating condition but this is only to illustrate the components; this position would not arise in use].

The lighting module 22 is a complete self-contained component for assembly into the blade by fitting to the main metal blade body 21 and fixing by the pivot connection 3,31. The electrical/electronic lighting module can then be tested before assembly. The stem surround portion 62 of the integrated moulded module casing component 6, meeting the power source housing portion 61 integrally at the join 63 in its top wall, protects the electrical components against damage during assembly and use, and against displacement in the blade. The drawing figures show this stem surround 62 partly broken away for illustrative reasons; it provides a continuous tube enclosing the connector wires 7 all the way along the stem from the power source housing 5 to the lamp 8 at its distal end.

The hinged cover 55 enables the batteries to be removed before disposal of the instrument, where regulations prohibit disposal of batteries.

An independent feature here is the laterally divergence of the step wall 264 forward of the opening 267 where the lighting module stem 221 projects through, providing a wider field of forward illumination while maintaining protection above the stem 221 from the upper flange 265. However, the skilled person will appreciate that the concepts described herein can be used in other blade forms.

The invention claimed is:

1. A laryngoscope comprising a handle, a blade and a light emitter on the blade;
    the blade having a tip end, a rear end and a blade body extending between the tip end and rear end, and the blade body having an underside and an upper side;
    the handle having a head, and the blade and handle being connected by a pivot connection between the rear end of the blade and the head of the handle, whereby the blade is pivotable relative to the handle between an operating position;
    the rear end of the blade defining a power source housing which houses a power source for the light emitter, the power source housing having a moveable cover operable to open or close an opening through which the power source can be removed from the housing, and
    wherein in the operating or extended position position of the blade, a portion of the head of the handle opposes the cover, or opposes a cover catch mechanism of the cover, to prevent opening of the cover.

2. A laryngoscope according to claim 1 in which the rear end of the blade comprises a rear end block formation in which the power source housing is defined, and which also comprises one or more connector formations for the connection of the blade to the handle.

3. A laryngoscope according to claim 2 in which a said connector formation of the rear end block is a pivot pin.

4. A laryngoscope according to claim 2 in which said connector formation of the rear end block is a catch formation and the handle head has a corresponding catch formation, said catch formations together constituting a catch mechanism engageable in the operating position of the blade to inhibit pivoting of the blade back to the folded position.

5. A laryngoscope according to claim 2 in which the handle head has opposed laterally spaced upstanding supports and the rear end block of the blade fits between these supports.

6. A laryngoscope according to claim 1 in which the housing has a housing wall and said cover comprises a moveable cover flap hinged to the housing wall, operable to open or close said opening through which one or more batteries as said power source as can be removed from the housing.

7. A laryngoscope according to claim 6 in which the moveable cover flap makes a cover catch engagement with the housing wall to hold it closed, and in the operating or extended position of the blade, a portion of the head of the handle opposes the cover catch mechanism to prevent opening of the moveable cover flap.

8. A laryngoscope according to claim 1 in which
    the rear end of the blade comprises a rear end block formation in which the power source housing is defined, and comprising a housing wall and said moveable cover,
    the rear end block formation having a bottom surface and a rear surface, part of said cover comprises the rear surface and part of said cover when closed comprises the bottom surface, and
    in the operating position, the bottom surface is in opposition to an upward surface of the handle head.

9. A laryngoscope according to claim 1 in which the blade comprises electrical connections between the power source and the light emitter.

10. A laryngoscope according to claim 9 in which the blade comprises a switch having an external movable switch actuator which engages the handle head in the operating position to move the actuator and switch on the light emitter.

11. A laryngoscope according to claim 1 in which the blade comprises a main blade body portion and a discrete lighting module fitted to the main blade body portion,
    the lighting module comprising the power source, the light emitter and a module casing, the module casing comprising
    a power source housing portion defining said power source housing, and
    a connector surround extending from the power source housing portion towards the light emitter, and enclosing connectors between the power source and the light emitter.

12. A laryngoscope comprising a handle and a blade pivotable relative to the handle between an operating position and a folded position;
    the handle having a head with opposed laterally spaced upstanding supports;
    the blade comprising a rear end block which fits between the upstanding supports of the handle head and is connected thereto by a pivoted connection, and comprises a power source housing containing a battery power source in the rear end of the blade;
    said housing having a cover which is openable for removal of the power source in the folded position of the laryngoscope, said cover comprising a cover flap which makes a cover catch engagement with a housing wall of the power source housing to hold it closed and in which, in the operating position of the laryngoscope, the cover catch engagement is opposed by a portion of the head of the handle to prevent disengagement thereof;

a light emitter on the blade; and lighting connections between the power source and the light emitter, and wherein the rear end block of the blade comprises a switch having an actuator which engages the handle head in the operating position of the laryngoscope to turn on the light emitter.

13. A laryngoscope according to claim 12 in which the blade comprises a main blade body portion and a discrete lighting module fitted to the main blade body portion, the lighting module comprising the power source, the light emitter and a module casing, the module casing comprising a power source housing portion defining said power source housing, and a connector stem extending from the power source housing portion and enclosing the lighting connections between the power source and the light emitter.

14. A laryngoscope comprising a handle, a blade and a light emitter on the blade;

the blade having a tip end, a rear end and a blade body extending between the tip end and rear end, and the blade body having an underside and an upper side;

the handle having a head, and the blade and handle being connected by a pivot connection between the rear end of the blade and the head of the handle, whereby the blade is pivotable relative to the handle between an operating position and a folded position;

the blade comprising a main blade body portion and a discrete lighting module fitted to the main blade body portion, the discrete lighting module comprising a power source, the light emitter and a module casing, the module casing comprising a power source housing portion defining a power source housing, and a connector stem extending from the power source housing portion to the light emitter and enclosing lighting connections between the power source and the light emitter, and in which the rear end of the blade has a rear end block formation which consists, in a lateral direction corresponding to the pivot axis of the pivot connection, partly of the power source housing portion of the module casing of the discrete lighting module, and partly of a rear portion of the main blade body portion.

15. A laryngoscope according to claim 14 in which the discrete lighting module comprises a switch mechanism, and an external actuator for the switch mechanism which engages the head of the handle in the operating position.

16. A laryngoscope according to claim 14 in which the main blade body portion comprises a pivot connector portion extending laterally across the power source housing to make the pivot connection across the width of the blade rear end block formation.

17. A laryngoscope blade having a tip end, a rear end and a blade body extending between the tip end and rear end, the blade body having an underside and an upper side;

the blade comprising a rear end block formation defining a power source housing to contain a power source in the rear end of the blade, the power source housing comprising a housing wall and having a movable cover flap hinged to the housing wall which is openable for insertion or removal of a said power source, the rear end block formation having a bottom surface and a rear surface, part of said cover flap when closed comprises the rear surface and part of said cover flap when closed comprises the bottom surface; and a pivot for connection between the rear end of the blade and the head of a handle, whereby the blade when connected to a said handle is pivotable relative to the handle between an operating position and a folded position, whereby in the operating position the bottom surface of the rear end block formation is in opposition to an upward surface of the handle head to prevent opening of the cover flap;

the blade further comprising a light emitter on the blade body, lighting connections between the power source housing and the light emitter, and a switch having an actuator to turn on the light emitter.

* * * * *